(12) United States Patent
Teshigawara (10) Patent No.: US 8,598,531 B2
(45) Date of Patent: Dec. 3, 2013

(54) RADIATION THERAPY APPARATUS AND CONTROL METHOD

(75) Inventor: Manabu Teshigawara, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/466,252

(22) Filed: May 8, 2012

(65) Prior Publication Data

US 2012/0253096 A1 Oct. 4, 2012

Related U.S. Application Data

(63) Continuation of application No. PCT/JP2011/069626, filed on Aug. 30, 2011.

(30) Foreign Application Priority Data

Aug. 30, 2010 (JP) ................................. 2010-192284

(51) Int. Cl.
*G01T 1/164* (2006.01)

(52) U.S. Cl.
USPC ..................................................... 250/363.03

(58) Field of Classification Search
USPC .................................. 250/363.01–363.1, 362
See application file for complete search history.

(56) References Cited

U.S. PATENT DOCUMENTS

2005/0201509 A1* 9/2005 Mostafavi et al. ............... 378/8
2006/0159220 A1* 7/2006 Heuscher ........................ 378/9

FOREIGN PATENT DOCUMENTS

| JP | 2007-107995 | 4/2007 |
|---|---|---|
| JP | 2010-94421 | 4/2010 |
| WO | WO 2010/046983 A1 | 4/2010 |

OTHER PUBLICATIONS

International Search Report mailed Oct. 4, 2011 in PCT/JP2011/069626 filed Aug. 30, 2011.
International Written Opinion mailed Oct. 4, 2011 in PCT/JP2011/069626 filed Aug. 30, 2011.
Extended European Search Report issued Apr. 23, 2013, in European Patent Application No. 11821810.6.

* cited by examiner

*Primary Examiner* — Kiho Kim
(74) *Attorney, Agent, or Firm* — Oblon, Spivak, McClelland, Maier & Neustadt, L.L.P.

(57) ABSTRACT

According to one embodiment, a radiation therapy apparatus includes a radiation irradiation device, a detector included in a PET scanner, a control unit, and a PET image reconstruction unit. The radiation irradiation device emits a therapeutic radiation. The detector counts light derived from gamma rays, and is provided with a gap portion through which the therapeutic radiation passes on a plane of rotation about the body axis of a subject. The control unit controls the radiation irradiation device and the detector so as to rotate in synchronization with each other in a state capable of emitting the therapeutic radiation to the gap portion. The PET image reconstruction unit reconstructs a PET image based on position information at the time of counting of the detector that nearly coincidentally counts pair annihilation gamma rays in a state where the control unit performs rotation control.

3 Claims, 10 Drawing Sheets

| MODULE ID | SCINTILLATOR NUMBER | ENERGY VALUE | DETECTION TIME |
|---|---|---|---|
| D1 | P11 | E11 | T11 |
| | P12 | E12 | T12 |
| | P13 | E13 | T13 |
| | ⋮ | ⋮ | ⋮ |
| D2 | P21 | E21 | T21 |
| | P22 | E22 | T22 |
| | P23 | E23 | T23 |
| | ⋮ | ⋮ | ⋮ |
| D3 | P31 | E31 | T31 |
| | P32 | E32 | T32 |
| | P33 | E33 | T33 |
| | ⋮ | ⋮ | ⋮ |
| ⋮ | ⋮ | ⋮ | ⋮ |

FIG.11

| COUNTING INFORMATION A | | | COUNTING INFORMATION B | | |
|---|---|---|---|---|---|
| SCINTILLATOR NUMBER | ENERGY VALUE | DETECTION TIME | SCINTILLATOR NUMBER | ENERGY VALUE | DETECTION TIME |
| P11 | E11 | T11 | P22 | E22 | T22 |
| P12 | E12 | T12 | P32 | E32 | T32 |
| P13 | E13 | T13 | P33 | E33 | T33 |
| ⋮ | ⋮ | ⋮ | ⋮ | ⋮ | ⋮ |

FIG.12

| SCINTILLATOR NUMBER | TIME INFORMATION | POSITION INFORMATION |
|---|---|---|
| P11 | T11 | (5, 4, 10) |
| | T12 | (5, 4, 9) |
| | T13 | (5, 3, 8) |
| | ⋮ | ⋮ |
| P12 | ⋮ | ⋮ |
| ⋮ | ⋮ | ⋮ |

RADIATION THERAPY APPARATUS AND CONTROL METHOD

CROSS-REFERENCE TO RELATED APPLICATIONS

This application is a continuation of PCT international application Ser. No. PCT/JP2011/069626 filed on Aug. 30, 2011 which designates the United States, and which claims the benefit of priority from Japanese Patent Application No. 2010-192284, filed on Aug. 30, 2010; the entire contents of which are incorporated herein by reference.

FIELD

Embodiments described herein relate generally to a radiation therapy apparatus and a control method.

BACKGROUND

Conventionally, positron emission computed tomography (PET) apparatuses are known as nuclear medicine imaging apparatuses that can make a functional diagnosis in body tissues of a subject.

Specifically, in a PET examination, a compound labeled with a positron-emitting radionuclide is administered to the subject. Such a PET apparatus coincidentally counts a pair of gamma rays (pair annihilation gamma rays) of 511 keV emitted in approximately opposite directions when a positron emitted from the labeled compound binds to an electron and annihilates by using a photon counting detector arranged around the subject. The PET apparatus then performs calculation processing on data of the gamma rays coincidentally counted (coincidence counting information) to reconstruct a PET image.

In recent years, radiation therapy for damaging a tumor has been performed by using a radiation irradiation device that emits a heavy particle beam as a therapeutic radiation. The heavy particle beam is a radiation generated by accelerating particles, such as a carbon ion, a neon ion, a silicon ion, and an argon ion, at high speed. The depth of penetration of the heavy particle beam into a human body is determined by energy supplied by an accelerator. Furthermore, the heavy particle beam releases energy inside the human body by colliding with an electron and an atomic nucleus in the path of travelling. In particular, the heavy particle beam releases energy drastically near the end of the path of travelling (Bragg peak), and stops. In other words, in the radiation therapy using the heavy particle beam, the Bragg peak is used to adjust the energy of the particles by the accelerator such that the particles stop at the portion of the tumor. As a result, it is possible to kill tumor cells alone while having a little influence on normal cells in the path of traveling.

In the radiation therapy using the heavy particle beam, a range (tumor site) determined by a treatment plan using various types of medical images, such as a PET image, an X-ray CT image, and an MRI image, is irradiated with the heavy particle beam. For example, the radiation irradiation device irradiates the range determined by the treatment plan with the heavy particle beam in multi-directions. Furthermore, also known as the radiation therapy using the heavy particle beam is intensity modulated radiation therapy (IMRT) in which, by performing irradiation of the heavy particle beam in any direction while modulating the magnitude of the heavy particle beam, the influence on the normal cells is reduced and the dose is concentrated within the outline of the tumor.

If the energy is equal to or higher than "511×2 keV", the heavy particle beam generates an electron and a positron by pair production in the path of travelling. The positron thus generated by pair production binds to an electron therearound and annihilates, whereby pair annihilation gamma rays are emitted. In other words, reconstructing a PET image by the PET apparatus in approximately real-time while performing the irradiation of the heavy particle beam by the radiation irradiation device allows a doctor to monitor whether the site determined by the treatment plan is irradiated with the heavy particle beam.

Therefore, PET apparatuses for radiation therapy monitoring have been developed in recent years. For example, a PET apparatus having two flat detectors arranged at positions facing each other with the subject interposed therebetween is known as such a PET apparatus for radiation therapy monitoring.

However, the conventional PET apparatus for radiation therapy monitoring described above fails to perform coincidence counting in all directions of a circumference about the subject, thereby deteriorating the image quality of PET images. Furthermore, in the conventional PET apparatus for radiation therapy monitoring described above, the irradiation angle of the heavy particle beam emitted from the radiation irradiation device is restricted.

DESCRIPTION OF EMBODIMENTS

First Embodiment

According to one embodiment, a radiation therapy apparatus includes an irradiation unit, a detector, a control unit, and an image reconstruction unit. The irradiation unit is configured to emit a therapeutic radiation. The detector is configured to count light derived from gamma rays, and is configured to be provided with a gap portion through which the therapeutic radiation emitted by the irradiation unit passes on a plane of rotation about a body axis of a subject. The control unit is configured to control the irradiation unit and the detector so as to rotate in synchronization with each other in a state capable of emitting the therapeutic radiation to the gap portion. The image reconstruction unit is configured to reconstruct a nuclear medicine image based on position information at time of counting of the detector that nearly coincidentally counts pair annihilation gamma rays emitted in association with release of energy of the therapeutic radiation emitted by the irradiation unit in a state where the control unit performs rotation control. Exemplary embodiments of a radiation therapy apparatus are described below in greater detail with reference to the accompanying drawings. In the description below, while the radiation therapy apparatus is explained by using an apparatus in which a radiation irradiation device that emits a heavy particle beam as a therapeutic radiation is arranged in a PET-CT apparatus as an example, it is not limited thereto. Alternatively, the apparatus in which the radiation irradiation device is arranged may be a PET apparatus or a PET-magnetic resonance imaging (MRI) apparatus, for example.

In the first embodiment, an explanation will be made of the case where the radiation irradiation device capable of performing intensity modulated radiation therapy (IMRT) in which irradiation of the heavy particle beam is performed in any direction while modulating the magnitude thereof is arranged in the PET-CT apparatus. However, the first embodiment can be applied to any apparatus that emits the heavy particle beam. Furthermore, the first embodiment in the description below can be applied to the case where a radiation other than the heavy particle beam, such as X-rays, is emitted from the radiation irradiation device, as long as pair annihilation gamma rays are emitted from the inside of an object to be irradiated in association with release of energy of the therapeutic radiation emitted from the radiation irradiation device.

Figure 1:
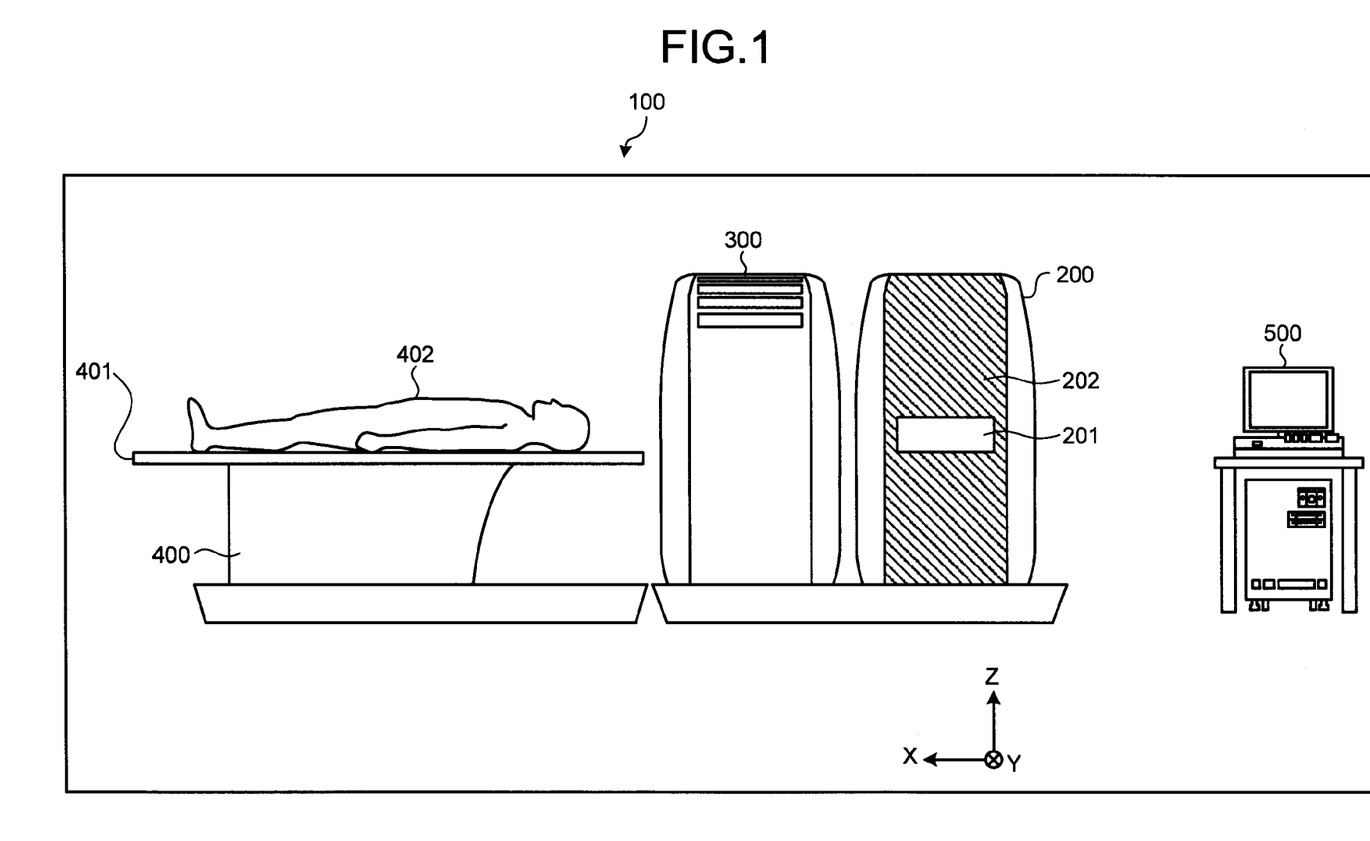
FIG. 1 is a diagram illustrating a whole image of a configuration of a PET-CT apparatus included in a radiation therapy apparatus according to a first embodiment.

FIG. 1 is a diagram illustrating a whole image of a configuration of the PET-CT apparatus included in the radiation therapy apparatus according to the first embodiment. In FIG. 1, 100 denotes a PET-CT apparatus, 200 denotes a PET scanner, 300 denotes an X-ray CT scanner, 400 denotes a bed, 401 denotes a tabletop on which a subject is lying, and 402 denotes the subject. As illustrated in FIG. 1, the PET-CT apparatus 100 includes the PET scanner 200, the X-ray CT scanner 300, the bed 400, and a console device 500. The X-direction in FIG. 1 represents a direction of the body axis of the subject 402 lying on the tabletop 401 illustrated in FIG. 1. The Y-direction represents a direction orthogonal to the X-direction on a horizontal plane. The Z-direction represents a vertical direction.

The bed 400 includes the tabletop 401 on which the subject 402 is lying. Furthermore, the bed 400 includes a bed control unit, which is not illustrated in FIG. 1, for moving the tabletop 401. The bed control unit is controlled by the console device 500, and moves the subject 402 lying on the tabletop 401 into an imaging bore of the PET-CT apparatus 100.

The PET scanner 200 includes a photon counting detector 210 (to be described later) that counts light derived from gamma rays for reconstructing a PET image. As illustrated in FIG. 1, in the PET scanner 200 according to the first embodiment, a gap portion 201 through which the heavy particle beam emitted by a radiation irradiation device 600, which will be described later, passes is provided to a plane of rotation about the body axis of the subject 402. The gap portion 201 is provided to both the detector 210 (to be described later) and a cover 202 arranged on the PET scanner 200. The cover 202 houses the detector 210 (to be described later). Furthermore, the cover 202 is capable of rotating about the body axis of the subject 402. In other words, the cover 202 is capable of rotating together with the detector 210 (to be described later).

Figure 2:
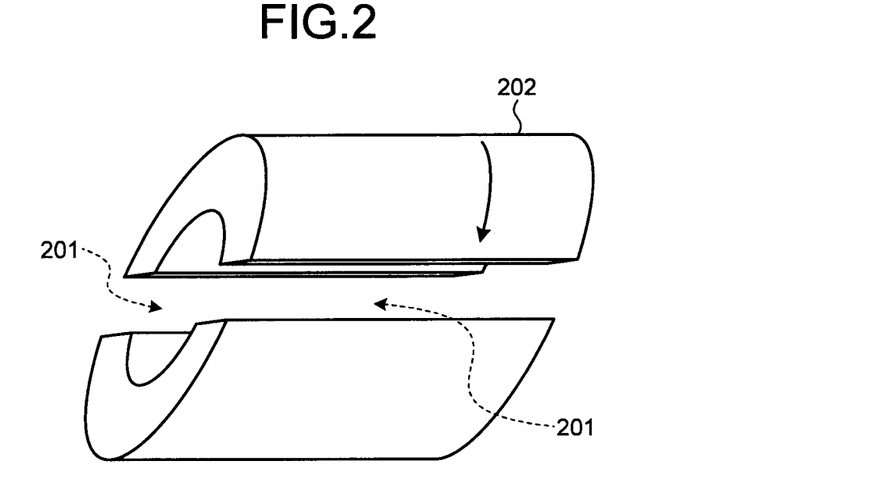
FIG. 2 is a diagram of an example of a gap portion in a PET scanner according to the first embodiment.

FIG. 2 is a diagram of an example of the gap portion in the PET scanner according to the first embodiment. In the example illustrated in FIG. 2, the cover 202 of the PET scanner 200 includes a plurality of gap portions at positions facing each other on the plane of rotation. In other words, the detector 210 (to be described later) includes a plurality of gap portions at positions facing each other on the plane of rotation.

Figure 3:
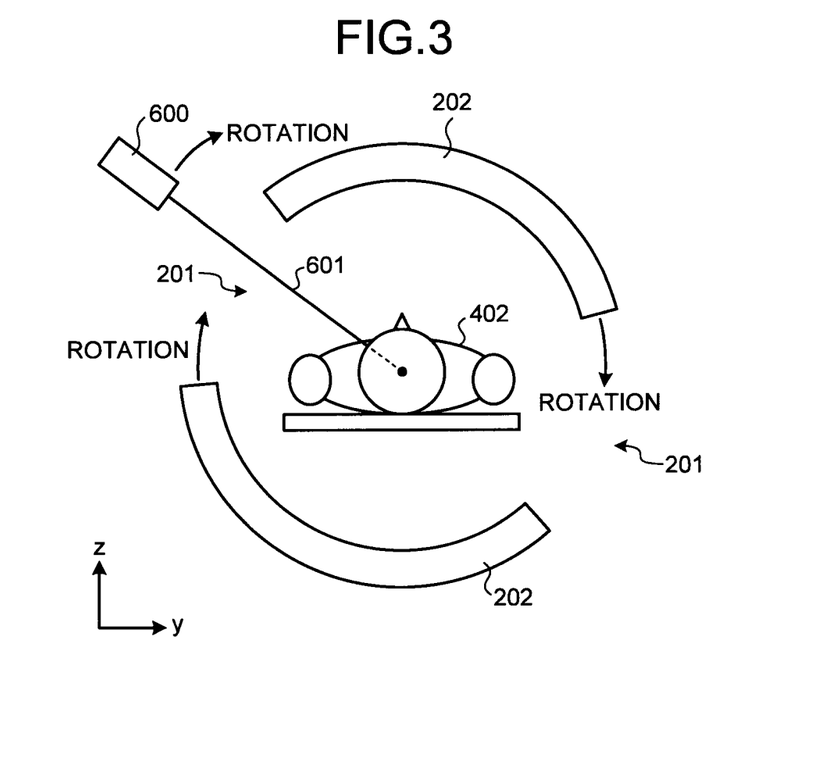
FIG. 3 is a diagram (1) of an example of a positional relationship between the PET scanner and a radiation irradiation device according to the first embodiment.
Figure 4:
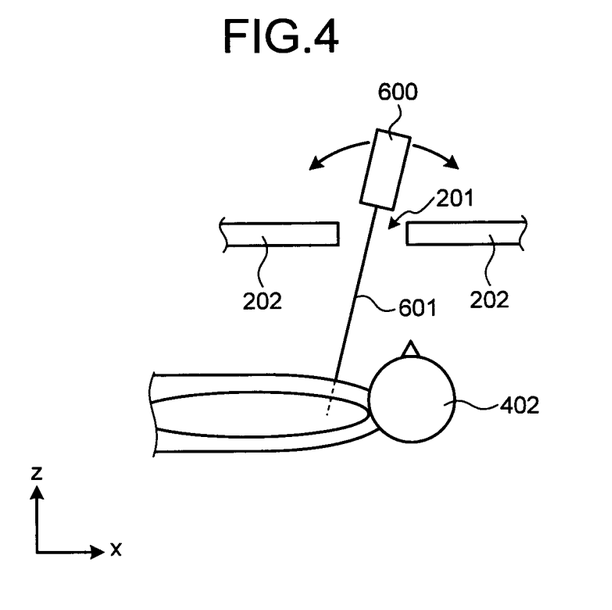
FIG. 4 is a diagram (2) of an example of the positional relationship between the PET scanner and the radiation irradiation device according to the first embodiment.

FIGS. 3 and 4 are diagrams of an example of a positional relationship between the PET scanner and the radiation irradiation device according to the first embodiment. As illustrated in FIG. 3, the radiation therapy apparatus according to the first embodiment is provided with the radiation irradiation device 600 that emits the heavy particle beam as the therapeutic radiation. The radiation irradiation device 600 is arranged so as to be capable of irradiating the subject 402 with the heavy particle beam through the gap portion of the cover 202 as illustrated in FIG. 3. A large part of a heavy particle beam 601 emitted by the radiation irradiation device 600 stops at an affected area of the subject 402 because of adjustment of energy by an accelerator, which is not illustrated.

The radiation irradiation device 600 and the cover 202 rotate in synchronization with each other by control of a control unit 540 in the console device, which will be described later, in a state capable of emitting the heavy particle beam to the gap portion 201. In the example illustrated in FIG. 3, the radiation irradiation device 600 and the cover 202 rotate in synchronization with each other in a clockwise direction viewed from the head of the subject 402. However, the first embodiment is not limited thereto, and the radiation irradiation device 600 and the cover 202 may rotate in synchronization with each other in a counterclockwise direction viewed from the head of the subject 402.

The radiation irradiation device 600 rotates in a manner maintaining the relative position to the plane of rotation of the cover 202. However, as illustrated in FIG. 4, the radiation irradiation device 600 can emit the heavy particle beam 601 from any position and in any direction with respect to the gap portion 201 of the cover 202.

As described above, in the radiation therapy apparatus according to the first embodiment, the radiation irradiation device 600 and the cover 202 of the PET scanner 200 can rotate in synchronization with each other. Therefore, it is possible to irradiate a three-dimensional irradiation site determined by a treatment plan with the heavy particle beam in any direction of 360 degrees.

The gamma rays detected by the detector 210 of the PET scanner 200 described above will now be explained. The PET scanner 200 includes a plurality of detectors 210 that detect the gamma rays for reconstructing a PET image. The detectors 210 are arranged in a ring shape around the body axis of the subject 402. The detectors 210, from outside of the body of the subject 402 lying on the tabletop 401, detects a pair of gamma rays (pair annihilation gamma rays) emitted from inside of the body of the subject 402, for example.

Specifically, every time the detector 210 counts the gamma rays, the PET scanner 200 collects the detection position indicating a position of the detector 210 that detects the gamma rays, the energy value at the time when the gamma rays are incident on the detector 210, and the detection time at which the detector 210 detects the gamma rays. The information collected by the PET scanner 200 is also referred to as "counting information". In the first embodiment, an explanation is made of the case where a time of flight (TOF) detector that collects, as the counting information, time of detection (absolute time) as the detection time of the gamma rays is used as the detector 210. Alternatively, in the first embodiment, a non-TOF detector that does not include time as the counting information may be used as the detector 210.

The detector 210 according to the first embodiment detects the pair annihilation gamma rays emitted from the subject 402 in association with release of energy of the heavy particle beam emitted from the radiation irradiation device 600. In other words, the detector 210 according to the first embodiment detects the pair annihilation gamma rays emitted from the subject 402 by emitting the heavy particle beam to the gap portion 201 from the radiation irradiation device 600. This causes the PET-CT apparatus 100 to reconstruct a PET image in which a path of the heavy particle beam is visualized.

The X-ray CT scanner 300 illustrated in FIG. 1 includes an X-ray tube 301 that emits X-rays for reconstructing an X-ray CT image and an X-ray detector 302 that detects the X-rays emitted by the X-ray tube 301. In the X-ray CT scanner 300, the X-ray tube 301 irradiates the subject 402 with the X-rays, and the X-ray detector 302 detects the X-rays passing through the subject 402. Specifically, the X-ray tube 301 emits the X-rays, and the X-ray detector 302 detects the X-rays while the X-ray CT scanner 300 is rotating about the body axis of the subject 402. In other words, the X-ray CT scanner 300 irradiates the subject 402 with the X-rays in multi-directions, and detects the attenuated X-rays absorbed in the subject 402 by passing through the subject 402 while being rotating about the body axis of the subject 402. Data generated by performing amplification processing, AD conversion processing, and the like on the X-rays detected by the X-ray detector 302 is also referred to as "X-ray projection data". The X-ray CT scanner 300 collects the X-ray projection data and the detection position at which the X-rays used for generating the X-ray projection data are detected.

Figure 5:
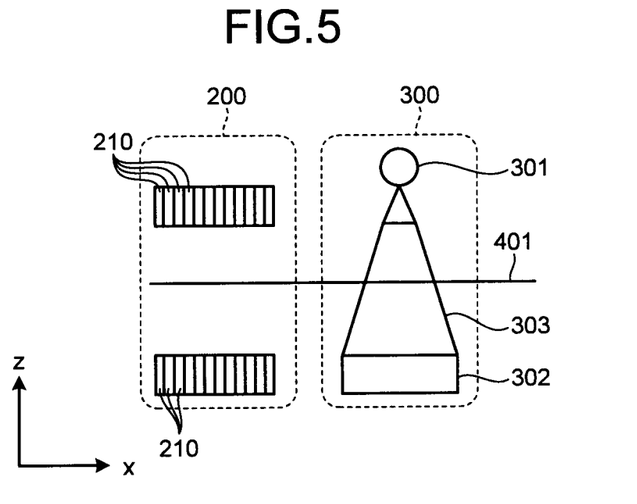
FIG. 5 is a diagram of an example of a positional relationship between the PET scanner and an X-ray CT scanner according to the first embodiment.

FIG. 5 is a diagram of an example of a positional relationship between the PET scanner and the X-ray CT scanner according to the first embodiment. FIG. 5 is a sectional view of the PET scanner 200 and the X-ray CT scanner 300 viewed in the Y-axis direction. The example illustrated in FIG. 5 depicts the case where not the gap portion 201 but the detectors 210 are present on the section of the PET scanner 200 and the X-ray CT scanner 300 viewed in the Y-axis direction. In FIG. 5, 200 denotes the PET scanner, 210 denotes the detector, 300 denotes the X-ray CT scanner, 301 denotes the X-ray tube, 302 denotes the X-ray detector, and 303 denotes the X-rays emitted by the X-ray tube 301. In FIG. 5, the tabletop 401 is illustrated in addition to the PET scanner 200 and the X-ray CT scanner 300 as a matter of convenience for explanation.

As illustrated in FIG. 5, in the PET scanner 200, a plurality of detectors 210 are arranged in the X-axis direction. Furthermore, the detectors 210 are arranged in a manner surrounding the body axis of the subject 402 in a ring shape. As illustrated in FIG. 5, the X-ray CT scanner 300 includes the X-ray tube 301 and the X-ray detector 302. The X-ray tube 301 and the X-ray detector 302 are arranged at positions facing each other with the tabletop 401 on which the subject 402 is lying at the time of measurement interposed therebetween.

Figure 6:
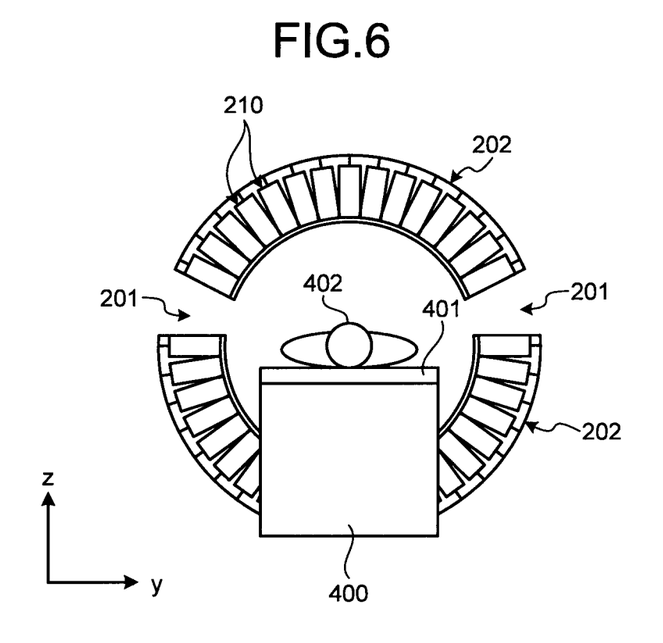
FIG. 6 is a diagram of a configuration of the PET scanner according to the first embodiment.

FIG. 6 is a diagram of a configuration of the PET scanner according to the first embodiment. In FIG. 6, 400 denotes the bed, 401 denotes the tabletop, 402 denotes the subject, 201 denotes the gap portion, 202 denotes the cover, and 210 denotes the detector. FIG. 6 is a sectional view of the PET scanner viewed in the X-axis direction. In FIG. 6, the subject 402, the bed 400, and the tabletop 401 are illustrated in addition to the PET scanner 200 as a matter of convenience for explanation.

As illustrated in FIG. 6, in the PET scanner 200, a plurality of detectors 210 are arranged in a manner surrounding the subject 402 in a ring shape. A photon counting detector, for example, is employed as the detector 210. Furthermore, as illustrated in FIG. 6, the PET scanner 200 includes the gap portion 201 in the plane of rotation. In the example illustrated in FIG. 6, the gap portion 201 is provided between the detectors 210 and in the cover 202.

Figure 7:
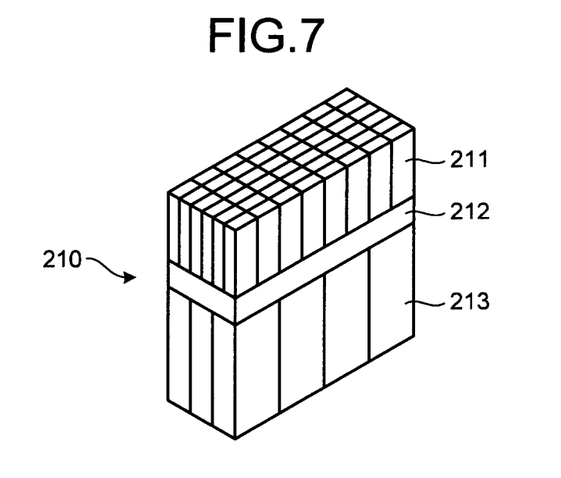
FIG. 7 is a diagram of an exemplary structure of a detector according to the first embodiment.

FIG. 7 is a diagram of an exemplary structure of the detector according to the first embodiment. In FIG. 7, 211 denotes scintillators, 212 denotes a light guide, and 213 denotes photo multiplier tubes (PMT).

As illustrated in FIG. 7, the detector 210 that counts light derived from the gamma rays includes the scintillators 211, the light guide 212, and the PMTS 213. The scintillator 211 converts the gamma rays emitted from the subject 402 and incident on the detector 210 into visible light, and outputs the visible light. The scintillator 211 is formed of, for example, NaI or BGO that converts gamma rays into visible light. Furthermore, as illustrated in FIG. 7, the scintillators 211 are arranged two-dimensionally. The visible light output by the scintillator 211 is also referred to as "scintillation light". The light guide 212 transmits the visible light output by the scintillator 211 to the PMT 213. The light guide 212 is formed of, for example, a plastic material having excellent optical transparency. The PMT 213 receives the visible light output by the scintillator 211 via the light guide 212, and converts the visible light thus received into an electrical signal. The PMT 213 is provided in plurality.

The PMT 213 will now be described in greater detail. The PMT 213 includes a photocathode that receives the scintillation light and generates a photoelectron, a multi-stage dynode that supplies an electric field in which the photoelectron generated by the photocathode is accelerated, and an anode from which an electron flows out. The electron released from the photocathode by the photoelectric effect is accelerated toward the dynode, and collides with the surface of the dynode to knock out a plurality of electrons. The phenomenon in which the electrons are knocked out on the surface of the dynode is repeated over the multi-stage dynode, thereby increasing the number of electrons in an avalanche manner.

If a piece of scintillation light is received, for example, the anode outputs approximately one million electrons. The number of electrons obtained from the anode in the case where a piece of scintillation light is received is also referred to as "gain of the PMT". In this case, the gain of the PMT 213 is "millionfold". Note that, when the number of electrons is increased in an avalanche manner, voltage of 1000 V or higher is generally applied between the dynode and the anode.

Thus, in the detector 210, the scintillator 211 converts the gamma rays into visible light, and the PMT 213 converts the visible light into an electrical signal. As a result, the detector 210 detects the gamma rays emitted from the subject 402.

Figure 8:
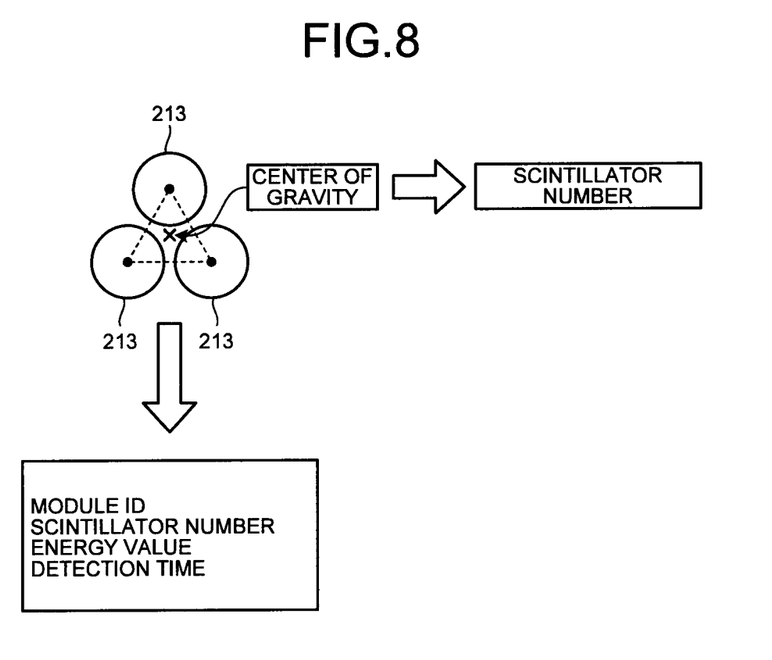
FIG. 8 is a diagram of information detected by an Anger-type detector according to the first embodiment.

As described above, every time the detector 210 detects the gamma rays, the PET scanner 200 collects the detection position, the energy value, and the detection time. A simple explanation will be made of an example of processing for calculating the detection position and the energy value in the case where the detectors 210 adjacent to one another detect the gamma rays coincidentally with reference to FIG. 8. FIG. 8 is a diagram of information detected by an Anger-type detector according to the first embodiment.

The PET scanner 200 performs Anger-type position calculation processing to determine the detection position, for example. Furthermore, if the PMT 213 is a position-detecting PMT, for example, the PET scanner 200 collects the detection position by using the position-detecting PMT 213. As illustrated in FIG. 8, an explanation will be made of the case where three PMTs 213 convert the scintillation light into electrical signals, and output the electrical signals at the same timing. In this case, the PET scanner 200 acquires the positions of the PMTs 213 that output the electrical signals coincidentally, and acquires the energy value of each of the electrical signals output from the PMTs 213 that output the electrical signals coincidentally. The PET scanner 200 then calculates the position of the center of gravity from the energy values thus acquired, and specifies the scintillator 211 corresponding to the position of the center of gravity thus calculated. Furthermore, the PET scanner 200 integrates the energy values of the electrical signals output by the PMTs 213 that convert the scintillation light into the electrical signals and output the electrical signals at the same timing, and determines the energy value obtained as a result of the integration to be the energy value of the gamma rays incident on the detector 210.

As illustrated in FIG. 8, every time the detector 210 detects the gamma rays, the PET scanner 200 collects a "scintillator number" that identifies the scintillator 211 uniquely, an "energy value", and "detection time". The example illustrated in FIG. 8 depicts the case where a "module ID" that is information uniquely identifying the detector 210 provided in plurality is also output in addition to the "scintillator number", the "energy value", and the "detection time".

The detector 210 collects the detection time with an accuracy of $10^{-10}$ seconds to $10^{-12}$ seconds, for example.

A simple explanation will be made of a processing flow in the case where the PET-CT apparatus 100 according to the first embodiment reconstructs a PET image and an X-ray CT image. In the PET-CT apparatus 100, the PET scanner 200 and the X-ray CT scanner 300 move from left to right, or the tabletop 401 and the bed 400 move from right to left in FIG. 1 and FIG. 5. As a result, the X-ray CT scanner 300 collects the X-ray projection data, and thereafter the PET scanner 200 collects the counting information. Subsequently, the console device 500 reconstructs a PET image and an X-ray CT image based on the information thus collected. However, the processing flow is not limited thereto, and the PET scanner 200 and the X-ray CT scanner 300 may move from right to left in FIG. 1 and FIG. 5.

Figure 9:
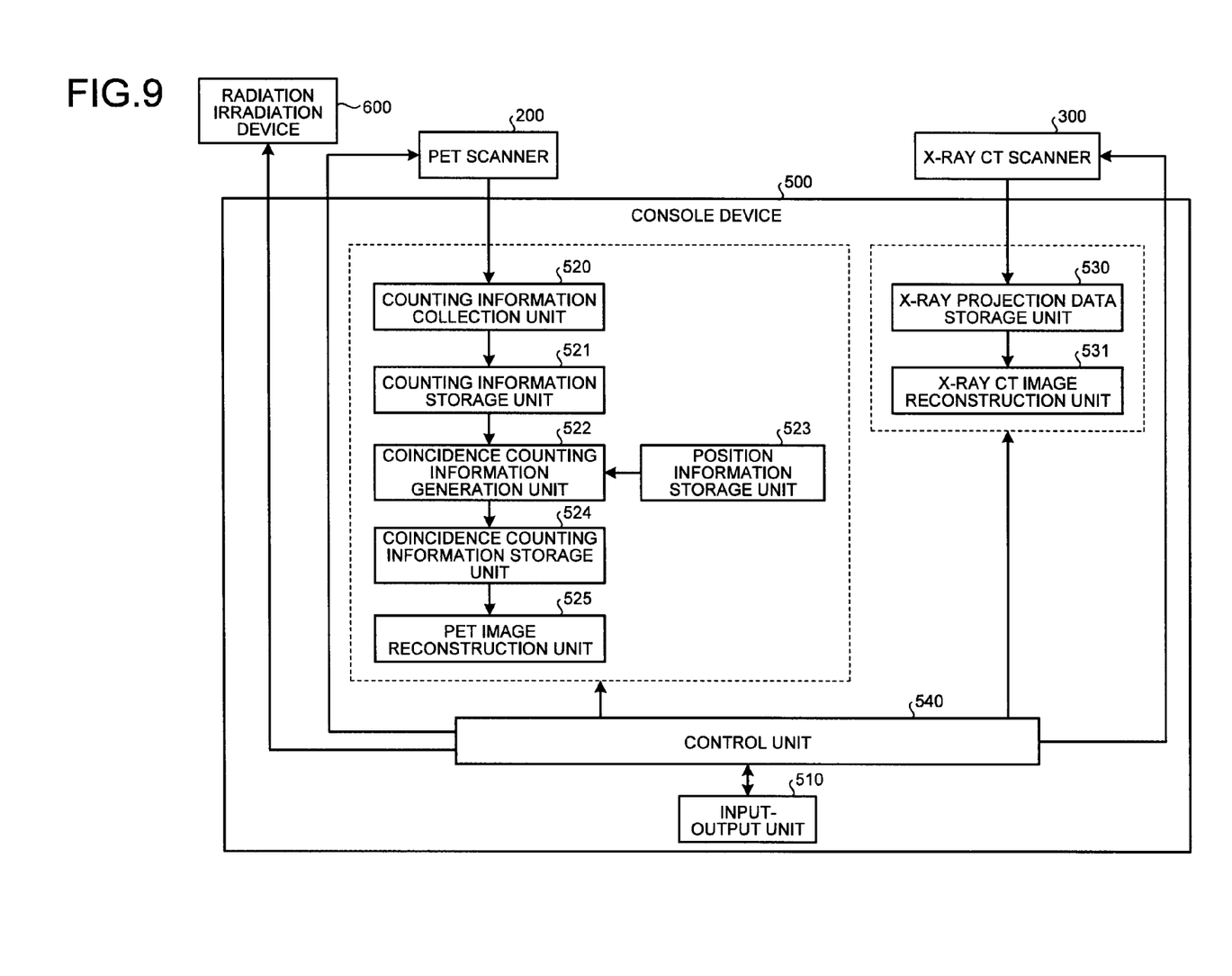
FIG. 9 is a block diagram of an exemplary configuration of a console device according to the first embodiment.

FIG. 9 is a block diagram of an exemplary configuration of the console device according to the first embodiment. The console device 500 reconstructs an X-ray CT image based on the information collected by the X-ray CT scanner 300. Furthermore, the console device 500 generates coincidence counting information by using the counting information collected by the PET scanner 200, and reconstructs a PET image based on the coincidence counting information thus generated. In the description below, the processing for reconstructing a PET image and the processing for reconstructing an X-ray CT image by the console device 500 may be performed by using an arbitrary method, and an explanation thereof will be made succinctly.

In the example illustrated in FIG. 9, the PET scanner 200, the X-ray CT scanner 300, and the radiation irradiation device 600 are illustrated in addition to the console device 500 as a matter of convenience for explanation. In the example illustrated in FIG. 9, the console device 500 includes an input-output unit 510 and the control unit 540. In addition, in the example illustrated in FIG. 9, the console device 500 includes an X-ray projection data storage unit 530 and an X-ray CT image reconstruction unit 531 so as to reconstruct an X-ray CT image. Furthermore, in the example illustrated in FIG. 9, the console device 500 includes a counting information collection unit 520, a counting information storage unit 521, a coincidence counting information generation unit 522, a position information storage unit 523, a coincidence counting information storage unit 524, and a PET image reconstruction unit 525 so as to reconstruct a PET image. In the first embodiment, an explanation is made of the case where one console device 500 reconstructs an X-ray CT image and a PET image. However, the first embodiment can be applied to the case where reconstruction of an X-ray CT image and reconstruction of a PET image are performed in different console devices.

The input-output unit 510 is connected to the control unit 540. The input-output unit 510 receives various types of instructions from a user who uses the radiation therapy apparatus, and transmits the various types of instructions thus received to the control unit 540. Furthermore, the input-output unit 510 receives information from the control unit 540, and outputs the information thus received to the user. The input-output unit 510 is, for example, a keyboard, a mouse, a microphone, a monitor, and a speaker. Explanations of details of the information and the instructions received by the input-output unit 510 and a detail of the information output by the input-output unit 510 are omitted herein. The explanations thereof will be made when each unit related thereto is described.

The control unit 540 includes an internal memory that stores therein a program specifying various types of processing processes and the like, and controls various types of processing. For example, the control unit 540 is an electronic circuit, such as an application specific integrated circuit (ASIC), a field programmable gate array (FPGA), a central processing unit (CPU), and a micro processing unit (MPU). The control unit 540 controls the whole processing of the radiation therapy apparatus. Specifically, the control unit 540 controls the PET scanner 200 and the X-ray CT scanner 300, thereby controlling radiography performed by the PET-CT apparatus 100. Furthermore, the control unit 540 controls the radiation irradiation device 600 so as to emit the heavy particle beam in multi-directions consecutively or intermittently in accordance with the treatment plan. Moreover, the control unit 540 controls the radiation irradiation device 600 and the detector 210 (cover 202) so as to rotate in synchronization with each other in a state capable of emitting the heavy particle beam to the gap portion 201.

The control unit 540 controls the reconstruction processing of a PET image and the reconstruction processing of an X-ray CT image in the console device 500. Furthermore, the control unit 540 displays a PET image, an X-ray CT image, a superimposed image of a PET image and an X-ray CT image, or the like on the monitor of the input-output unit 510.

The X-ray projection data storage unit 530 stores therein X-ray projection data transmitted from the X-ray CT scanner 300. The X-ray CT image reconstruction unit 531 performs back projection processing on the X-ray projection data stored in the X-ray projection data storage unit 530 by the filtered back projection (FBP) method, for example, thereby reconstructing an X-ray CT image.

The counting information collection unit 520 collects counting information from counting results output by the detectors 210, and stores the counting information in the counting information storage unit 521. In other words, the counting information collection unit 520 sequentially receives the counting information collected by the PET scanner 200, and stores the counting information thus received in the counting information storage unit 521. The counting information collection unit 520 may be included in the PET scanner 200.

Figure 10:
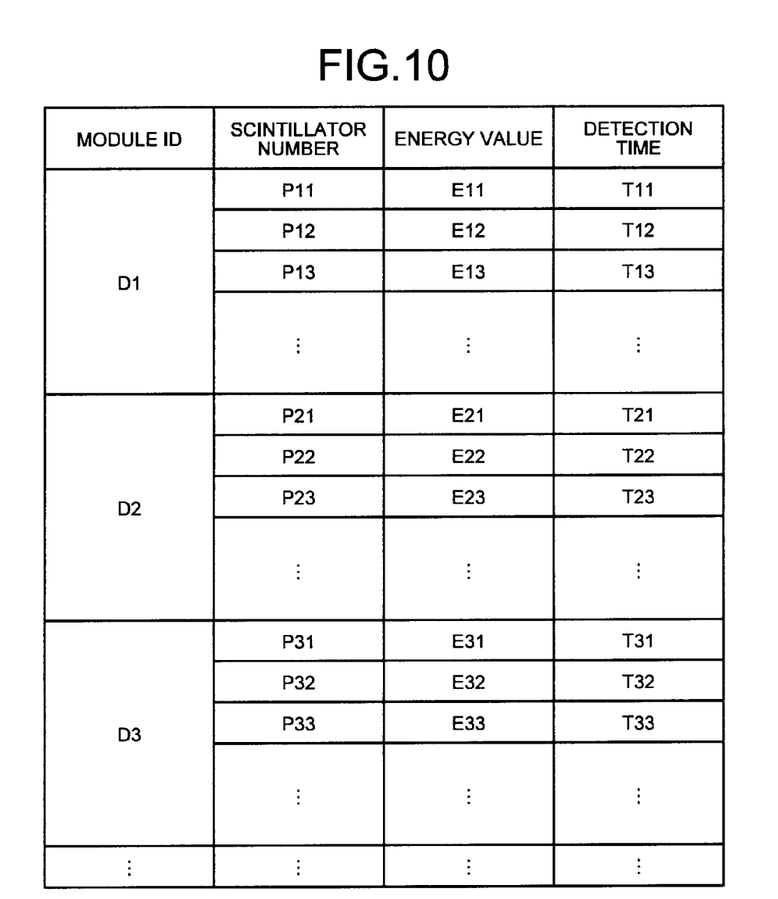
FIG. 10 is a diagram of an example of counting information stored in a counting information storage unit according to the first embodiment.

The counting information storage unit 521 stores therein the counting information stored by the counting information collection unit 520. For example, the counting information storage unit 521 is a semiconductor memory device, such as a random access memory (RAM) and a flash memory, or a storage device, such as a hard disk and an optical disk. FIG. 10 is a diagram of an example of the counting information stored in the counting information storage unit 521 according to the first embodiment.

In the example illustrated in FIG. 10, the counting information storage unit 521 stores therein the "scintillator number", the "energy value", and the "detection time" in a manner corresponding to the "module ID". The "module ID" is the information uniquely identifying the detector 210 provided in plurality.

In the example illustrated in FIG. 10, the counting information storage unit 521 stores therein, in a manner corresponding to a module ID "D1", a scintillator number "P11", an energy value "E11", and detection time "T11", and a scintillator number "P12", an energy value "E12", and detection time "T12". In other words, the counting information storage unit 521 stores therein the fact that the scintillator "P11" detects gamma rays of the energy value "E11" at the detection time "T11" in the detector "D1", and the fact that the scintillator "P12" detects gamma rays of the energy value "E12" at the detection time "T12" in the detector "D1". Furthermore, the counting information storage unit 521 stores therein the counting information based on counting results output by other detectors 210 in the same manner as described above.

Referring back to FIG. 9, the coincidence counting information generation unit 522 generates a combination of two pieces of counting information whose difference in detection time is within a time window among the counting information stored in the counting information storage unit 521 as coincidence counting information obtained by counting pair annihilation gamma rays nearly coincidentally.

Specifically, the coincidence counting information generation unit 522 generates the coincidence counting information based on conditions of coincidence counting information generation specified by an operator. The conditions of coincidence counting information generation include the time window, for example. The time window indicates an upper limit of difference between two detection times in the case where a pair of gamma rays are both counted.

For a pair of gamma rays emitted coincidentally from a positron-emitting radionuclide, the detection times of the gamma rays each included in the pair of gamma rays are the same, or difference between the two detection times is small even if the detection times are not the same. As a result, the coincidence counting information generation unit 522 uses the time window to prevent false coincidence counting information from being generated.

For example, an explanation will be made of the case where the coincidence counting information generation unit 522 generates the coincidence counting information by using a time window of "10 nanoseconds". In this case, the coincidence counting information generation unit 522 refers to the "detection time (T)" of each "module ID", and searches for a combination of the counting information whose difference between two detection times is within a "time window of 10 nanoseconds" among the modules.

Searching for a combination in which the detection time is within the time window is also referred to as "coincidence finding". A list of the coincidence counting information generated by the coincidence counting information generation unit 522 is also referred to as a "coincidence list".

An energy window may be set as the conditions of coincidence counting information generation. The energy value of a pair of gamma rays emitted by annihilation of a positron is already specified in advance. For example, 18F, 15O, and 11C each emit gamma rays of "511 keV". Therefore, any gamma rays emitted coincidentally from a positron-emitting radionuclide have an energy value within a predetermined range. As a result, the coincidence counting information generation unit 522 uses the energy window to exclude counting information not of the pair of gamma rays emitted from the positron-emitting radionuclide, and generates the coincidence counting information. Thus, the coincidence counting information generation unit 522 can prevent false coincidence counting information from being generated. As described above, setting the conditions of coincidence counting information generation makes it possible to perform random correction for excluding accidental coincidence counting, scatter correction for preventing counting information of scattered gamma rays from being generated as the coincidence counting information, sensitivity correction for correcting difference in sensitivity among the detectors 210, and other correction.

Figure 11:
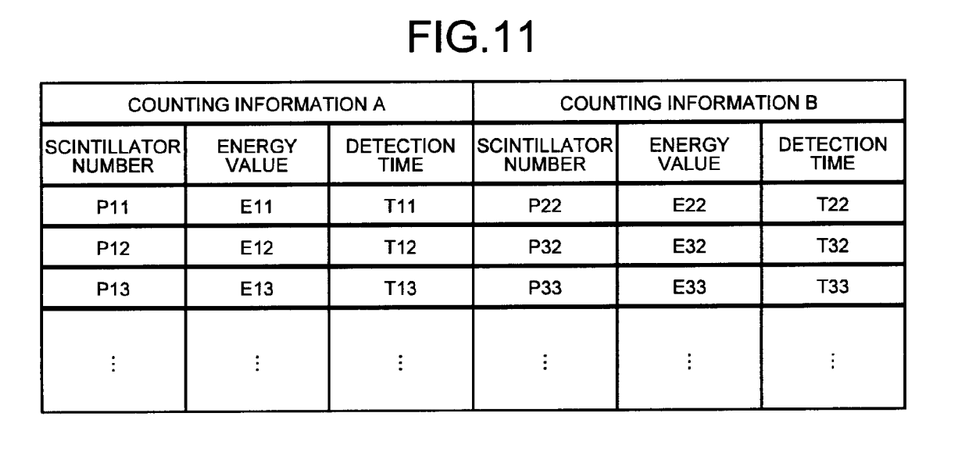
FIG. 11 is a diagram of an example of coincidence counting information stored in a coincidence counting information storage unit according to the first embodiment.

The coincidence counting information generation unit 522 then stores the coincidence counting information thus generated in the coincidence counting information storage unit 524. For example, the coincidence counting information storage unit 524 is a semiconductor memory device, such as a RAM and a flash memory, or a storage device, such as a hard disk and an optical disk. FIG. 11 is a diagram of an example of the coincidence counting information stored in the coincidence counting information storage unit according to the first embodiment.

As illustrated in FIG. 11, the coincidence counting information storage unit 524 stores therein a combination of two pieces of counting information. In FIG. 11, two pieces of counting information included in the combinations of the counting information are referred to as "counting information A" and "counting information B", respectively, as a matter of convenience for description. In the example illustrated in FIG. 11, the coincidence counting information storage unit 524 stores therein a combination of the counting information A including the scintillator number "P11", the energy value "E11", and the detection time "T11", and of the counting information B including a scintillator number "P22", an energy value "E22", and detection time "T22". In other words, the coincidence counting information storage unit 524 stores therein the fact that the scintillator "P11" detects one of pair annihilation gamma rays emitted from the subject 402 in association with release of energy of the heavy particle beam at the detection time "T11". In addition, the coincidence counting information storage unit 524 stores therein the fact that the scintillator "P22" detects the other of the pair annihilation gamma rays emitted from the subject 402 in association with the release of energy of the heavy particle beam at the detection time "T22".

Referring back to FIG. 9, the PET image reconstruction unit 525 reads the coincidence counting information generated by the coincidence counting information generation unit 522 from the coincidence counting information storage unit 524, and uses the coincidence counting information thus read to reconstruct a PET image. Specifically, the PET image reconstruction unit 525 considers the coincidence counting information to be projection data of the gamma rays, and reconstructs the PET image from the projection data of the gamma rays by using a successive approximation method. The successive approximation methods include a maximum likelihood expectation maximization (MLEM) method, and an ordered subset MLEM (OSEM) method in which the convergence time is significantly shortened by improving the algorithm of the MLEM method.

In the first embodiment, however, the detectors 210 rotate in association with the irradiation of the heavy particle beam. Therefore, the PET image reconstruction unit 525 according to the first embodiment reconstructs the PET image based on position information at the time of counting of the detector 210 that nearly coincidentally counts pair annihilation gamma rays emitted in association with release of energy of the heavy particle beam emitted from the radiation irradiation device 600 in a state where the control unit 540 performs rotation control.

In other words, the PET image reconstruction unit 525 uses the information in which the scintillator number in the coincidence counting information is corrected to a position at the time of actual counting, thereby reconstructing the PET image.

Figure 12:
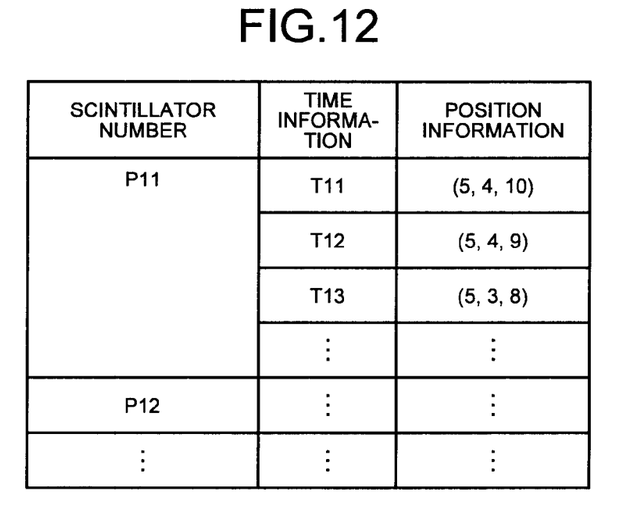
FIG. 12 is a diagram of an example of position information stored in a position information storage unit according to the first embodiment.

An example of the processing will be described below. The coincidence counting information generation unit 522, for example, uses the position information storage unit 523 illustrated in FIG. 9 to correct the coincidence counting information. FIG. 12 is a diagram of an example of position information stored in the position information storage unit according to the first embodiment.

The position information storage unit 523 stores therein the position information indicating a position of the detector 210 in a manner corresponding to time information indicating time. In the example illustrated in FIG. 12, the position information storage unit 523 stores therein the time information and the position information in a manner corresponding to the scintillator number. The position information storage unit 523, for example, stores therein time information "T11" and position information "5, 4, 10" in a manner corresponding to the scintillator number "P11". Note that the numbers included in the position information "5, 4, 10" represent coordinates on the X-axis, the Y-axis, and the Z-axis, respectively. In other words, the position information storage unit 523 stores therein the fact that the scintillator "P11" is present at the position information "5, 4, 10" at the time "T11". Similarly, the position information storage unit 523 stores therein the position information at other times, and also stores therein the time information and the position information for other scintillators 211 in the same manner as described above.

The example illustrated in FIG. 12 depicts the case where the position information storage unit 523 stores therein the time information and the position information in a manner corresponding to the scintillator number. However, the first embodiment is not limited thereto. The position information storage unit 523, for example, may store therein the position information and the time information in a manner corresponding to identification information for identifying the detector 210. Alternatively, if the detection position in space coordinates in which the subject 402 is present can be specified, the position information storage unit 523 may store therein the position information and the time information in a manner corresponding to arbitrary information. Furthermore, the example illustrated in FIG. 12 depicts the case where coordinates on the X-axis, the Y-axis, and the Z-axis are used as the position information. However, the first embodiment is not limited thereto, and arbitrary information may be used.

The position information stored in the position information storage unit 523 is supplied, for example, from the control unit 540 that performs the rotation control of the radiation irradiation device 600 and the detector 210 in accordance with the treatment plan. The control unit 540, for example, generates the position information such as the example illustrated in FIG. 12 based on the initial position and the rotation speed of the detector 210, and stores the position information thus generated in the position information storage unit 523.

Subsequently, the coincidence counting information generation unit 522 uses the position information stored in the position information storage unit 523, and corrects the scintillator number in the coincidence counting information thus generated to the position (coordinates) at the time of the counting. The coincidence counting information generation unit 522 then stores the coincidence counting information thus corrected in the coincidence counting information storage unit 524. The PET image reconstruction unit 525 then reads the coincidence counting information in which the position information is corrected from the coincidence counting information storage unit 524, and reconstructs a PET image. The PET image reconstructed by the PET image reconstruction unit 525 is displayed on the monitor of the input-output unit 510 by control of the control unit 540.

Figure 13:
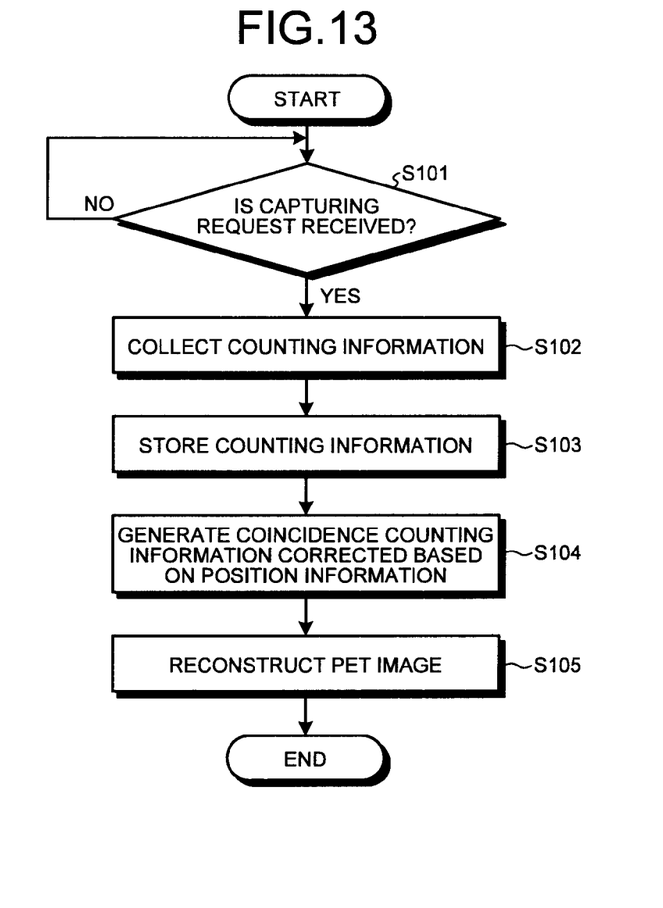
FIG. 13 is a flowchart illustrating an example of a flow of PET image capturing processing performed by the radiation therapy apparatus according to the first embodiment.

An example of a flow of PET image capturing processing performed by the radiation therapy apparatus according to the first embodiment will now be described with reference to FIG. 13. FIG. 13 is a flowchart illustrating the example of the flow of the PET image capturing processing performed by the radiation therapy apparatus according to the first embodiment. It is to be noted that the PET-CT apparatus 100 captures an X-ray CT image prior to the series of processing described below. Furthermore, when the PET image is captured, the control unit 540 controls the radiation irradiation device 600 and the detectors 210 so as to rotate in synchronization with each other in a state capable of emitting the heavy particle beam to the gap portion 201 as described above. The control unit 540 can change the direction of emitting the heavy particle beam to the gap portion 201 arbitrarily in accordance with the treatment plan during rotation of the radiation irradiation device 600 (refer to FIG. 4).

As illustrated in FIG. 13, in the PET-CT apparatus 100 that constitutes the radiation therapy apparatus, if a capturing request is received from the user (YES at Step S101), the control unit 540 operates the PET scanner 200, and the PET scanner 200 collects counting information (Step S102). In other words, every time the gamma rays are detected, the PET scanner 200 collects the detection position, the energy value, and the detection time.

The counting information collection unit 520 then receives the counting information collected by the PET scanner 200, and stores the counting information in the counting information storage unit 521 (Step S103). Subsequently, the coincidence counting information generation unit 522 generates coincidence counting information from the counting information stored in the counting information storage unit 521, and generates coincidence counting information obtained by correcting the scintillator number based on the position information stored in the position information storage unit 523 (Step S104).

The PET image reconstruction unit 525 then reconstructs a PET image by using the coincidence counting information thus corrected (Step S105), and the processing is terminated.

As described above, according to the first embodiment, the radiation irradiation device 600 emits the heavy particle beam as a therapeutic radiation. The detector 210 counts light derived from the gamma rays, and is provided with the gap portion 201 through which the heavy particle beam emitted by the radiation irradiation device 600 passes on the plane of rotation about the body axis of the subject 402. The control unit 540 controls the radiation irradiation device 600 and the detector 210 so as to rotate in synchronization with each other in a state capable of emitting the heavy particle beam to the gap portion 201. The PET image reconstruction unit 525 reconstructs a PET image based on position information at the time of counting of the detector 210 that nearly coincidentally counts pair annihilation gamma rays emitted in association with release of energy of the heavy particle beam emitted from the radiation irradiation device 600 in a state where the control unit 540 performs rotation control.

In other words, in the first embodiment, even when a PET image obtained by extracting a site irradiated with the heavy particle beam is captured, the site can be irradiated with the heavy particle beam in any direction. Furthermore, in the first embodiment, the coincidence counting can be performed in all directions of the circumference about the subject. In other words, in the first embodiment, the image quality of the PET image can be made uniform. Accordingly, in the first embodiment, it is possible to confirm the site irradiated with the heavy particle beam accurately while ensuring the degree of freedom for the irradiation angle of the heavy particle beam.

Furthermore, according to the first embodiment, the PET scanner 200 includes a plurality of gap portions 201 at positions facing to each other on the plane of rotation. In other words, in the first embodiment, it is possible to prevent the case from occurring in which the heavy particle beam does not stop in the body, and is detected by the detector 210. As a result, in the first embodiment, it is possible to prevent noise from being generated in the PET image, and to confirm the site irradiated with the heavy particle beam reliably.

Second Embodiment

Other embodiments may be realized in addition to the first embodiment. In the description below, another embodiment will be explained.

In the first embodiment, the explanation has been made of the case where, after the coincide counting information is generated, the correction processing of the scintillator number is performed by using the position information. In the embodiment, however, the detection position of the gamma rays in the coincidence counting information used for reconstruction of a PET image only need to reflect the position of the detector 210 at the time of the counting. The counting information collection unit 520, for example, may correct the scintillator number in the counting information to the coordinates at the time of the counting. Furthermore, in the PET scanner 200, the scintillator number in the counting information may be corrected to the coordinates at the time of the counting.

Furthermore, the correction processing of the position information may be performed by referring to the table described above. Alternatively, the correction processing of the position information may be performed by using the information of the rotation speed, and calculating the detection position (position at the time of the counting) from the detection time.

Figure 14:
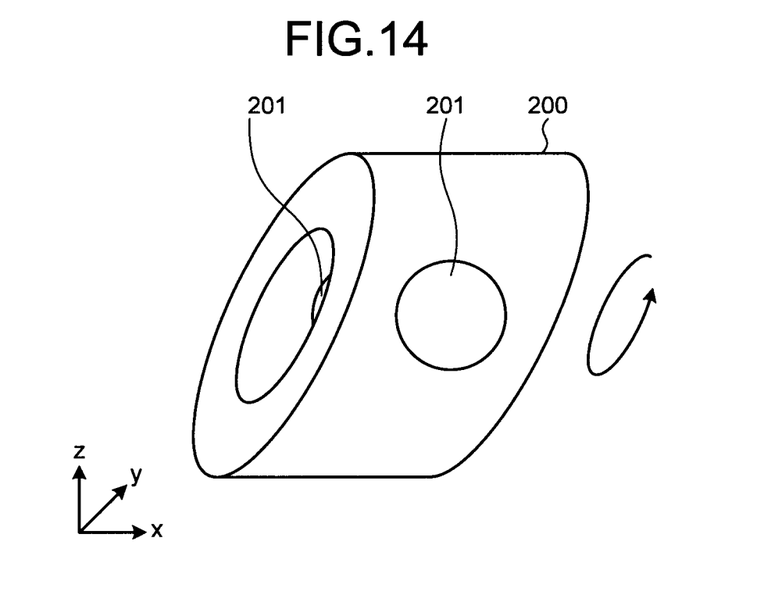
FIG. 14 is a diagram (1) of an example of the gap portion.
Figure 15:
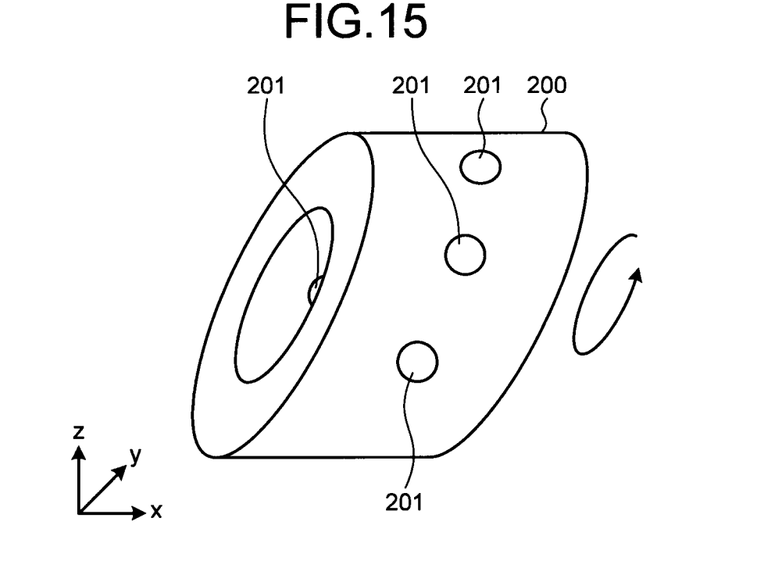
FIG. 15 is a diagram (2) of another example of the gap portion.

In the first embodiment, for example, the explanation has been made of the case where two gap portions 201 in a rectangular-shape are provided to the PET scanner 200. However, the embodiment is not limited thereto, and the gap portion 201 may be provided in any shape and in any number. As illustrated in FIG. 14, for example, the shape of the gap portion 201 may be a circle, an ellipse, or an arbitrary shape. Furthermore, as illustrated in FIG. 15, the number of the gap portions 201 may be three or more, and an arbitrary number. Alternatively, the number of the gap portions 201 may be one. FIG. 15 illustrates the case where the number of the gap portions 201 is four. FIG. 14 and FIG. 15 are diagrams of examples of the gap portion.

Figure 16:
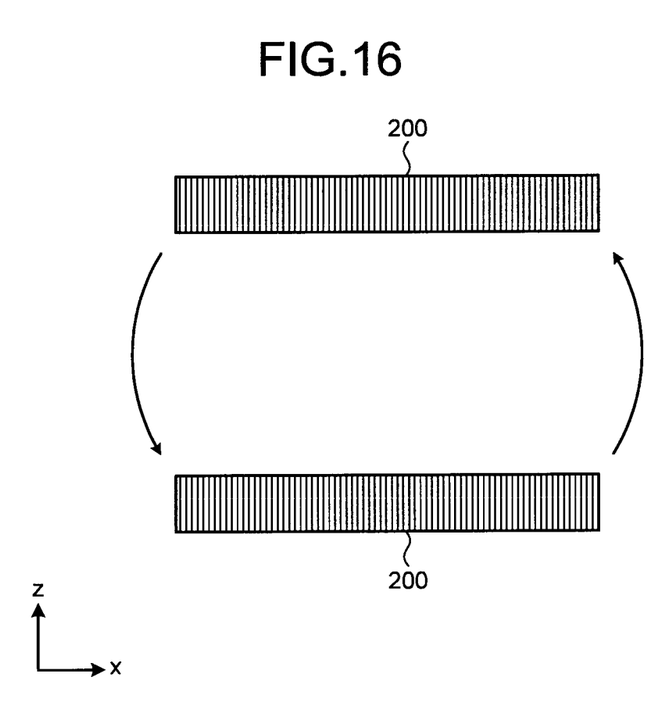
FIG. 16 is a diagram of an example of the PET scanner.

In the first embodiment, for example, the explanation has been made of the case where the detectors 210 are arranged in a ring shape in the PET scanner 200. However, the embodiment is not limited thereto. As long as being capable of rotating in synchronization with the radiation irradiation device 600, the detectors 210 may be arranged in a flat form as illustrated in FIG. 16, for example, or in an arbitrary shape. FIG. 16 is a diagram of an example of the PET scanner. FIG. 16 is a sectional view of the PET scanner 200 viewed in the Z-axis direction.

In the first embodiment, for example, the explanation has been made of the case where the console device 500 receives the counting information from the PET scanner 200 to use the counting information. However, the embodiment is not limited thereto. The console device 500, for example, may receive the detection result obtained by the detectors 210 from the PET scanner 200. In this case, the console device 500 receives waveform data output from the PMTs 213, and generates the counting information from the waveform data thus received.

In the first embodiment, for example, the explanation has been made of the case where the console device 500 receives the counting information from the PET scanner 200 to generate the coincidence counting information. However, the embodiment is not limited thereto. The PET scanner 200, for example, may generate the coincidence counting information from the counting information, and transmit the coincidence counting information thus generated to the console device 500.

Among the processing described in the first embodiment, all or a part of processing explained to be performed automatically may be performed manually, or all or a part of processing explained to be performed manually may be performed automatically by a known method. In addition, the processing process, the control process, the specific names, the information including various types of data and parameters illustrated in the specification and the drawings (FIG. 1 to FIG. 16) can be changed arbitrarily if not otherwise specified.

Each component in each device is illustrated as a functional concept, and is not necessarily to be physically configured as illustrated. In other words, a specific aspect of distribution and integration of each device is not limited to the illustrated aspect, and may be configured by distributing and integrating all or a part thereof functionally or physically in arbitrary units in accordance with various types of loads and usage.

The control method performed by the radiation therapy apparatus described in the first embodiment can be realized by executing a control program prepared in advance by a computer, such as a personal computer and a work station. Furthermore, the control program may be recorded in a computer-readable recording medium, such as a hard disk, a flexible disk (FD), a CD-ROM, an MO, and a DVD, and be executed by being read from the recording medium by the computer.

As described above, according to the first embodiment and the second embodiment, it is possible to confirm the site irradiated with the heavy particle beam accurately while ensuring the degree of freedom for the irradiation angle of the heavy particle beam.

While certain embodiments have been described, these embodiments have been presented by way of examples only, and are not intended to limit the scope of the invention. Indeed, the novel embodiments described herein may be embodied in a variety of other forms; furthermore, various omissions, substitutions, and changes in the form of the apparatus and method described herein may be made without departing from the spirit of the invention. The accompanying claims and their equivalents are intended to cover such forms or modifications as would fall within the scope and spirits of the invention.

What is claimed is:

1. A radiation therapy apparatus, comprising:
    an irradiation unit configured to emit therapeutic radiation;
    a detector configured to count light derived from gamma rays, and configured to be provided with a gap portion through which the therapeutic radiation emitted by the irradiation unit passes on a plane of rotation about a body axis of a subject;
    a control unit configured to perform rotation control to control the irradiation unit and the detector to rotate in synchronization with each other while the irradiation unit emits the therapeutic radiation to the gap portion; and
    an image reconstruction unit configured to reconstruct a nuclear medicine image based on position information at a time of counting of the detector that nearly coincidentally counts pairs of annihilation gamma rays emitted in association with release of energy of the therapeutic radiation emitted by the irradiation unit in a state where the control unit performs the rotation control.

2. The radiation therapy apparatus according to claim 1, wherein the detector comprises a plurality of gap portions at positions facing each other on the plane of rotation.

3. A control method, comprising:
    controlling, by a control unit performing rotation control, an irradiation unit that emits therapeutic radiation and a detector, which counts light derived from gamma rays and is provided with a gap portion through which the therapeutic radiation emitted by the irradiation unit passes on a plane of rotation about a body axis of a subject, to rotate in synchronization with each other while the irradiation unit emits the therapeutic radiation to the gap portion; and
    reconstructing, by an image reconstruction unit, a nuclear medicine image based on position information at a time of counting of the detector that nearly coincidentally counts pairs of annihilation gamma rays emitted in association with release of energy of the therapeutic radiation emitted by the irradiation unit in a state where the control unit performs the rotation control.

* * * * *